(12) United States Patent
Weltmann et al.

(10) Patent No.: US 10,124,080 B2
(45) Date of Patent: Nov. 13, 2018

(54) HAND DISINFECTION DEVICE HAVING A PLASMA AND AEROSOL GENERATOR

(71) Applicants: Wilfried Kroemker, Bueckeburg (DE); Leibniz-Institut fuer Plasmaforschung und Technologie e.V., Greifswald (DE)

(72) Inventors: Klaus-Dieter Weltmann, Osteebad Binz (DE); Manfred Stieber, Greifswald (DE); Thomas Von Woedtke, Sundhagen (DE); Wilfried Kroemker, Bueckeburg (DE)

(73) Assignee: Leibniz-Institut fuer Plasmaforschung und Technologie e.V., Greifswald (DE)

( * ) Notice: Subject to any disclaimer, the term of this patent is extended or adjusted under 35 U.S.C. 154(b) by 240 days.

(21) Appl. No.: 14/916,748

(22) PCT Filed: Sep. 5, 2014

(86) PCT No.: PCT/EP2014/068919
§ 371 (c)(1),
(2) Date: Mar. 4, 2016

(87) PCT Pub. No.: WO2015/032888
PCT Pub. Date: Mar. 12, 2015

(65) Prior Publication Data
US 2016/0220714 A1    Aug. 4, 2016

(30) Foreign Application Priority Data

Sep. 6, 2013    (DE) .................. 10 2013 109 777

(51) Int. Cl.
*A61L 2/14*    (2006.01)
*A61L 2/22*    (2006.01)
*A61L 2/00*    (2006.01)

(52) U.S. Cl.
CPC ............... *A61L 2/0011* (2013.01); *A61L 2/14* (2013.01); *A61L 2/22* (2013.01); *A61L 2202/21* (2013.01)

(58) Field of Classification Search
CPC ...................................... A61L 2/22; A61L 2/14
See application file for complete search history.

(56) References Cited

U.S. PATENT DOCUMENTS 3,918,987 A * 11/1975 Kopfer .................... A61H 35/00
                                                  134/113
5,945,068 A * 8/1999 Ferone .................... E03C 1/057
                                                  134/102.3

(Continued)

FOREIGN PATENT DOCUMENTS

DE    10 2011 003 782 A1    8/2012
DE    10 2012 003 557 A1    8/2013

(Continued)

*Primary Examiner* — Donald R Spamer
(74) *Attorney, Agent, or Firm* — W&C IP

(57) ABSTRACT

The invention relates to a disinfection device (1) for plasma disinfection of surfaces comprising a plasma generator (2) for generating a disinfecting plasma gas stream (PA), and comprising an at least partially closed disinfection area (5) that is in communicating connection with the plasma generator (2), which is configured for receiving the surface (6) to be disinfected. The disinfection device (1) has an aerosol generator (9) for generating an aqueous aerosol stream (A) containing particles. The aerosol generator (9) is in communicating connection with the plasma generator (2) in order to guide the plasma gas stream (PA) mixed with the aerosol stream (A) in the disinfection area (5) onto the surface (6) to be disinfected.

16 Claims, 6 Drawing Sheets

(56) References Cited

U.S. PATENT DOCUMENTS

| | | | |
|---|---|---|---|
| 6,706,243 B1* | 3/2004 | Sias | A61L 2/14 |
| | | | 134/102.2 |
| 2010/0201007 A1* | 8/2010 | Tsuda | F24F 6/06 |
| | | | 261/83 |
| 2013/0272929 A1 | 10/2013 | Pelfrey et al. | |

FOREIGN PATENT DOCUMENTS

| | | |
|---|---|---|
| EP | 2 223 704 A1 | 9/2010 |
| WO | 00/67805 | 11/2000 |
| WO | 2011/023478 A1 | 3/2001 |
| WO | 2010/066667 A1 | 6/2010 |
| WO | 2011/018423 A2 | 2/2011 |
| WO | 2012/018891 A2 | 2/2012 |
| WO | 2014/135254 A1 | 9/2014 |

\* cited by examiner

HAND DISINFECTION DEVICE HAVING A PLASMA AND AEROSOL GENERATOR

The invention relates to a disinfection device for plasma disinfection of surfaces, with a plasma generator for generating a disinfecting plasma gas stream and with an at least partly closed disinfection region which is communicatively connected to the plasma generator and which is embodied to receive the surface to be disinfected.

Disinfection solutions which e.g. are applied to the hands to be disinfected are used to disinfect surfaces, in particular to disinfect the hand in medical apparatuses.

EP 2 223 704 A1 describes an apparatus for disinfecting e.g. hands using a non-thermal plasma, which flows into a housing open on one side.

Furthermore, WO 2011/023478 A1 has disclosed the practice of undertaking a two-dimensional treatment of regions of human or animal skin or mucous membrane surfaces with cold plasmas at atmospheric pressure in order to treat disease in this manner. An electrode system for generating a surface dielectric barrier discharge consists, firstly, of flexible materials which can cling to curved surfaces and, secondly, of an outer, electrically conductive surface which is used as a grounded electrode and structured in such a way that surface dielectric barrier discharges can form in the interstices of the structure that remain free. As a result of the embodiment as a clinging cuff, the treated area is covered and therefore protected against drying out.

WO 2011/018423 A2 discloses a method and a device for treating living cells by means of a plasma, wherein apparatuses for mixing and transporting active ingredients to influence the metabolism of the cells are furthermore provided in addition to the apparatuses for generating a plasma. As a result, it is possible to let substances act on living cells by means of a plasma. As a result of the interaction between plasma and tissue, there is a change in the composition of lipid structures such that the entry of topically applied substances into the region of living cells is briefly made possible.

U.S. Pat. No. 6,706,243 B1 discloses a device for cleaning hands in which, optionally, a plasma gas stream can be guided into a hand cleaning space. Additionally, the hands are cleaned under pressure by way of an air stream guided through an ion source. A cleaning solution is pumped into a gas stream. The gas stream mixed with the cleaning solution is atomized and guided into the plasma generator.

Proceeding herefrom, it is an object of the present invention to provide an improved disinfection device for plasma disinfection of surfaces and an improved method for plasma disinfection of surfaces, which enable a more efficient and skin-friendly disinfection of cells and tissues in particular.

The object is achieved by the disinfection device with the features of claim 1 and by the plasma disinfection method with the features of claim 13. Advantageous embodiments are described in the dependent claims.

What is proposed is that the disinfection device has an aerosol generator for generating an aerosol stream containing aqueous particles, wherein the aerosol generator is communicatively connected to the plasma generator in order to guide the plasma stream mixed with the aerosol stream onto the surface to be disinfected in the disinfection region.

By the mixing of aqueous aerosol particles with a plasma stream and the simultaneous surface disinfection using the plasma stream containing aqueous aerosol particles, carrying out the disinfection of, in particular, skin tissue in a very gentle and effective manner with high process reliability is successful. It was found that it was possible, beyond the simple plasma disinfection of skin tissue, to also apply e.g. care products by way of the aqueous aerosol particles, which reduce the damaging influence of the plasma on the skin and have a caring effect and at the same time contribute to an efficient disinfection process with high process reliability.

The aerosol stream and the plasma gas stream are preferably selected in such a way that the pH-value of the aqueous aerosol particles incident on the surface to be disinfected is influenced. The influence should preferably be exercised in such a way that the pH-value, which otherwise lies by distilled water in the region of pH 5 to 6, is displaced in the direction of the acidic region. By way of example, an aerosol which itself also has a disinfecting effect is feasible. However, it is particularly advantageous if pure water without any additives such as cleaning solutions, fragrances or care products is used as a fluid for the aerosol stream. This results in an expedient pH-range which is not too acidic, i.e. lies in the region of approximately 3.5 to 4.

Care products or fragrances can be applied independently of the plasma gas stream mixed with water aerosols (comprising water vapor), preferably after the plasma treatment in terms of time. As a result of this, it is possible to counteract the ozone smell of the treated surface and additionally care for the surface, e.g. by means of a hand cream. The supply is preferably realized in the treatment space above the supply region for the plasma gas stream, i.e. adjacent to the opening for inserting the surface to be treated. The nozzle openings for introducing fragrances and/or care products by way of nozzles are thus disinfected (sterilized) at the same time during the plasma treatment.

It is particularly advantageous if the aerosol generator has an atomizer unit for atomizing a liquid. In particular, such a liquid can be an emulsion-containing liquid such as e.g. emulsions with skin-care substances. By atomizing such an emulsion-containing liquid, mixing the skin-care substances with the plasma stream into a form suitable in conjunction with the plasma disinfection and applying it onto the surface to be disinfected is successful.

It is particularly advantageous if the atomizer unit has an ultrasonic atomizer. Surprisingly, it was found that sufficiently small droplet sizes could be generated by means of such an ultrasonic atomizer; these bring about an improved disinfection and care effect in conjunction with the plasma stream. In the case of ultrasound atomization, the mean droplet size is less than 5 µm and it is particularly preferably approximately 2 to 4 µm on average. These mean values are established from the droplet size which sets-in as a maximum in at least 60% and preferably in at least 80% of the measured droplets. In addition to the very small droplet size, an ultrasonic atomizer also has the effect of generating aerosols with a high viscosity. This also contributes to an improved disinfection effect in conjunction with a plasma stream. Therefore, an improved interaction of the aerosols with the plasma stream is successful due to the ultrasonic atomization and, overall, there is an improved result of the surface disinfection. However, such an aerosol quality may, under certain circumstances, also be obtained by a different type of atomization, e.g. by a mechanical atomization.

By way of example, molecular moistening of the plasma gas stream is advantageous. This can be achieved by means of a moistened humidification surface, at which an air stream for moistening sweeps past. This air stream is preferably the plasma gas stream itself.

The aerosol generator is preferably coupled to the plasma gas stream outlet of the plasma generator. Then, the plasma gas stream generated by the plasma generator is mixed with the aerosol stream of the aerosol generator and guided into the disinfection region. As a result, the aerosols are not adversely affected by the plasma generator itself. In particular, what this avoids is that the generated plasma is quenched by the water/air mixture in the plasma generator, i.e. that the intensity of the plasma is significantly reduced by aqueous particles or the plasma is partly extinguished and therefore loses the effectiveness thereof. In this case, it is particularly advantageous if the plasma gas stream is guided through the volume of the aerosol generator as this ensures a sufficient residence time which ensures a modification of the aerosols by means of the plasma gas stream. In this respect, the volume and the flow rate should be matched to one another.

It was found that a higher degree of effectiveness in terms of the disinfection is obtained by such guidance of the plasma gas stream through the aerosol generator than when aerosols are guided through the plasma.

The degree of effectiveness of the plasma gas stream can be increased by virtue of the gas stream (air stream) supplied to the plasma generator being pre-dried. To this end, an air dryer (e.g. a cartridge filled with silica gel) is disposed upstream of the inlet of the plasma generator.

It was found to be advantageous if the gas mass flux for the plasma gas is set to approximately 2 to 20 standard liters per minute, i.e. 2-20 slpm or 3.3775 to 33.775

$$\frac{Pa \cdot m^3}{s}.$$

The amount of aerosol should then be approximately 0.5 to 5 ml/min. The ratio of plasma gas to amount of aerosol is preferably in the region of approximately 400 to 1 to 40 000 to 1.

The frequency of the aerosol generator should preferably be more than 100 kHz. It was found that the disinfection result could be improved with a higher frequency of the ultrasonic atomizer of more than 850 kHz. Preferably, the frequency lies in the range from 1200 kHz to 3000 MHz.

The plasma generator should be supplied with voltage at a frequency in the region of approximately 400 Hz to 27.12 MHz of the high voltage, or with DC voltage.

The disinfection device preferably has a fan (or a pump such as e.g. a membrane pump), which is communicatively connected to the disinfection region in order to guide an air stream into the disinfection region. This air stream can be the aerosol-containing plasma stream which is forced to flow into the disinfection region by means of the fan. However, it is also conceivable that an additional air stream is guided into the disinfection region in addition to the aerosol-containing plasma stream.

It is particularly advantageous if the fan (or pump) is connected to a heating apparatus for heating the air stream caused by the fan. In this way, the effective temperature on the surface to be disinfected is increased, which improves the disinfecting effect of the aerosol-containing plasma stream.

The fan (or pump) is particularly advantageously in communicating connection with the plasma generator for guiding an air stream caused by the fan through the plasma generator. By way of the plasma generator, this air stream is converted into a plasma stream which is mixed with aerosols.

The disinfection region is preferably embodied to receive at least one hand to be disinfected of a person and to disinfect the surface of the hand at least received in the disinfection region. Hence, the disinfection method is suitable for hand disinfection in a particularly advantageous manner, which e.g. needs to be carried out at regular intervals by clinical staff in hospitals. A further field of use lies in other comparable installations, in which there are increased demands for hygiene, such as in e.g. restrooms, public pools, medical practices etc. Such a disinfection device enables a fast, reliable and skin-friendly disinfection of the hand, in which care substances are also applied contactlessly to the skin with the aid of the aerosols. The contactless hand disinfection in the disinfection region also ensures a disinfection of regions that are difficult to access, independently of individual cleaning procedures of the individual persons. As a result, a hand disinfection that is reliable and has high process reliability can be achieved.

After the introduction of the surface to be disinfected, the disinfection region should be closed-off to the best possible extent in order to ensure a reliable surface treatment without being disturbed under standard conditions. To this end, it is advantageous if the otherwise closed-off disinfection region has an opening for introducing the surface to be disinfected, e.g. a hand, which opening is closed-off from the surroundings with the aid of at least one air curtain. The air curtain is formed by an air stream guided through air nozzles. In this respect, air knives are advantageously suitable, in the case of which the emerging air assumes a narrow and sufficiently broad form and brings about an air curtain with approximately the same length at the start and end. The air gap preferably lies in the region between 0.5 and 0.8 mm.

Below, the invention is explained in more detail on the basis of exemplary embodiments with the attached drawings. In detail:

Figure 1:
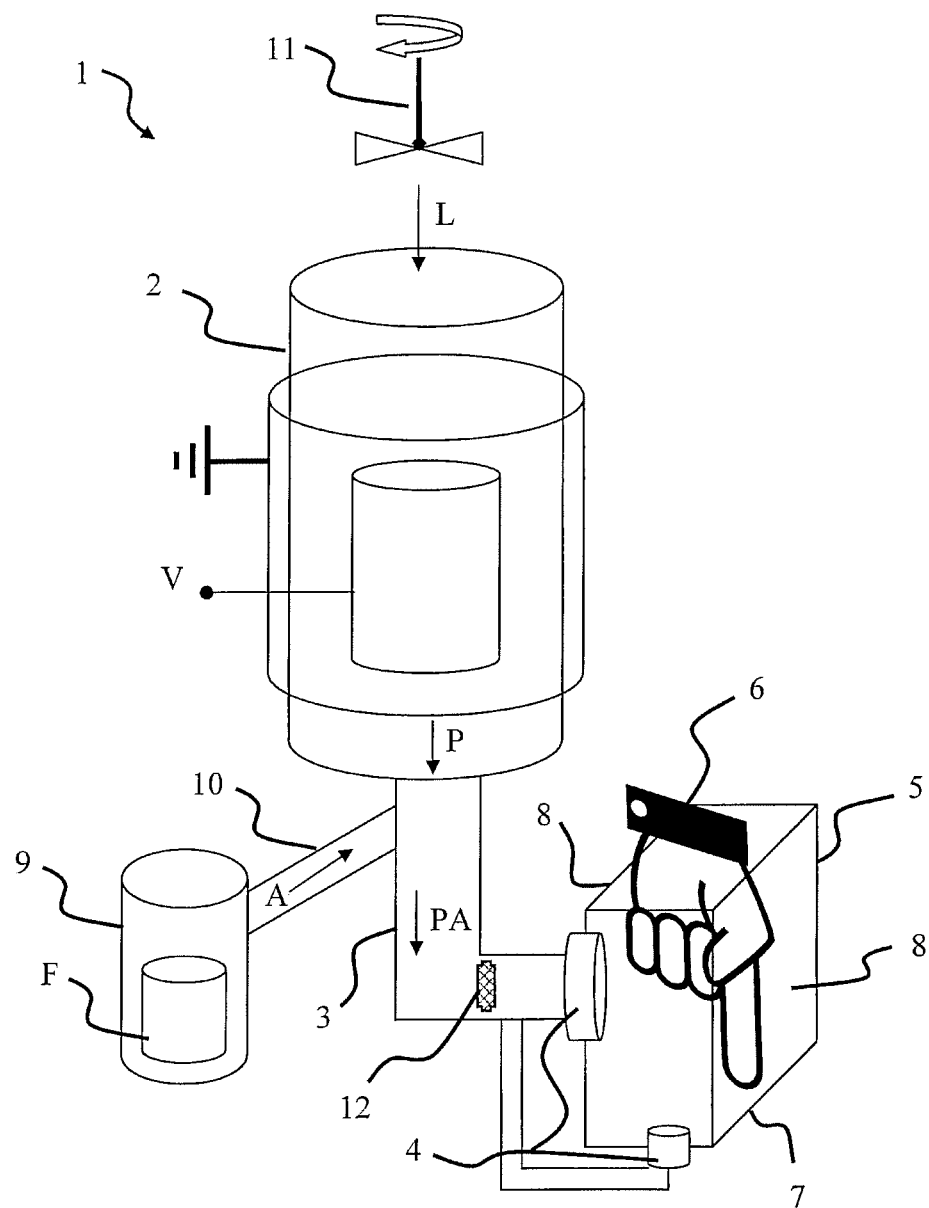
FIG. 1 shows a sketch of a first embodiment of a disinfection device for plasma disinfection of surfaces.

In FIG. 1, it is possible to identify a sketch of a first embodiment of a disinfection device 1 for plasma disinfection of surfaces, in particular of human hands 6 of a person. The disinfection device 1 has a plasma generator 2, by means of which a disinfecting plasma gas stream P is generated. By way of a plasma supply line 3 and nozzles 4, the plasma gas stream P is introduced into a disinfection region 5 in which the surface to be disinfected, such as the hand 6 of a person, can be held. The disinfection region 5 is preferably embodied as a container open only on one side, the side walls 8 of which container have the nozzles 4. It is also conceivable that further nozzles 4 are present in the base 7 of the disinfection region 5. The disinfection region 5 is preferably rectangular with side walls 8 lying relatively closely next to one another, between which the flat hand 6 can be inserted.

What becomes clear, furthermore, is that an aerosol generator 9, preferably in the form of an ultrasonic atomizer, is switched into the plasma supply line 3 at the outlet of the plasma generator 2. By way of an aerosol line 10, the outlet of the aerosol generator 2 is communicatively connected to the plasma line 3 at the outlet of the plasma generator 2. In this way, an aerosol stream A, which is generated by atomizing a fluid F by way of the ultrasonic atomizer, can be mixed with the plasma stream P. This aerosol-containing plasma stream P is then introduced into the disinfection region 5 by way of the nozzles 4.

The flow required herefor is generated with the aid of a fan 11, which is communicatively connected to the inlet of the plasma generator 2 in order to guide an air stream L into the inner space of the plasma generator 2. The plasma generator 2 then converts this air stream L into a plasma gas stream PA.

By way of example, a plasma ion source for generating a dielectric barrier discharge, as is sufficiently well known per se from the prior art, may serve as plasma generator 2. Plasma generators 2 generating a non-thermal plasma are particularly suitable. It is also conceivable for the plasma generators 2 to use surface DBD sources or volume DBD sources (DBD=dielectric barrier discharge). Alternatively, a plasma generator 2 on the basis of a plasma jet method is also conceivable. Jet-like plasmas, arc plasmas, plasma torches, plasmas excited capacitively or inductively in or near the normal pressure range and plasmas generated by corona discharge are also possible.

Non-thermal plasma generally contains ozone is therefore oxidizing. Non-thermal plasma is therefore particularly suitable for a surface disinfection.

By way of example, the plasma generator can have two (e.g. tube-shaped) electrodes lying within one another, with a high voltage V being applied to one of said electrodes and the other electrode being connected to ground potential.

The aerosol generator 9 is preferably embodied as an ultrasonic atomizer. The aerosols A generated by such an aerosol generator 9 preferably have a mean particle size in the range of at most 15 μm and preferably at most 12 μm. The mean particle size is preferably in the range from 1 to 15 μm and particularly preferably in the range from 4 to 12 μm. Larger surfaces of the aerosol particles are disadvantageous in that these take up more ozone and therefore significantly reduce the effect of the plasma stream P and PA.

Optionally, a heating apparatus 12 can be introduced additionally into the air and/or plasma stream L and P, respectively, or even into the aerosol-containing plasma stream PA. As a result, a suitable temperature can be achieved by cooling the plasma gas stream P or, optionally, by heating.

Figure 2:
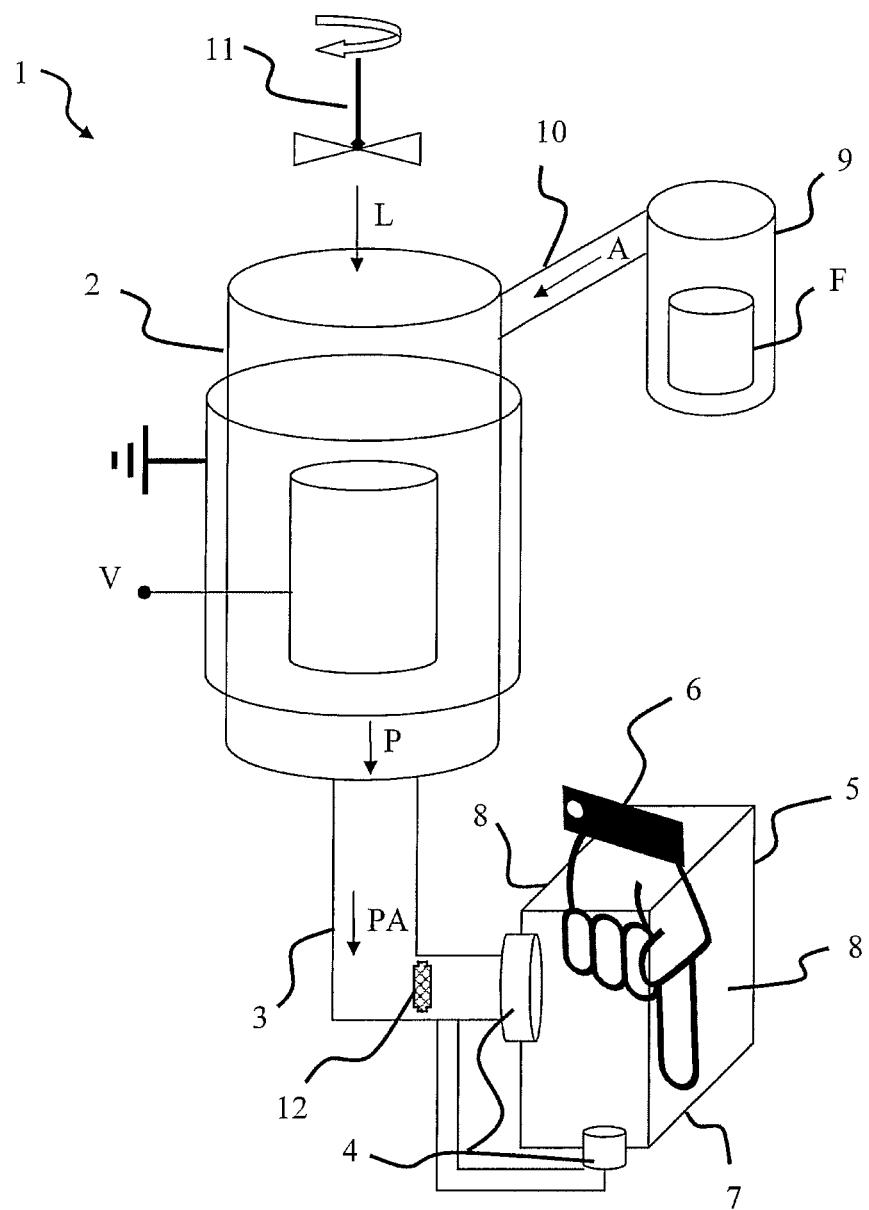
FIG. 2 shows a sketch of a second embodiment of a disinfection device for plasma disinfection.

In FIG. 2, it is possible to identify a second embodiment of the disinfection device 1. It is comparable to the first embodiment of the disinfection device 1, and so reference can substantially be made to what was said above. In contrast to the first embodiment, the aerosol generator 9 is coupled to the inlet of the plasma generator 2. As a result, the aerosol stream A at the inlet region of the plasma generator 2 is mixed with the air stream L and converted into an aerosol-containing plasma gas stream PA by way of the plasma generator 2.

Figure 3:
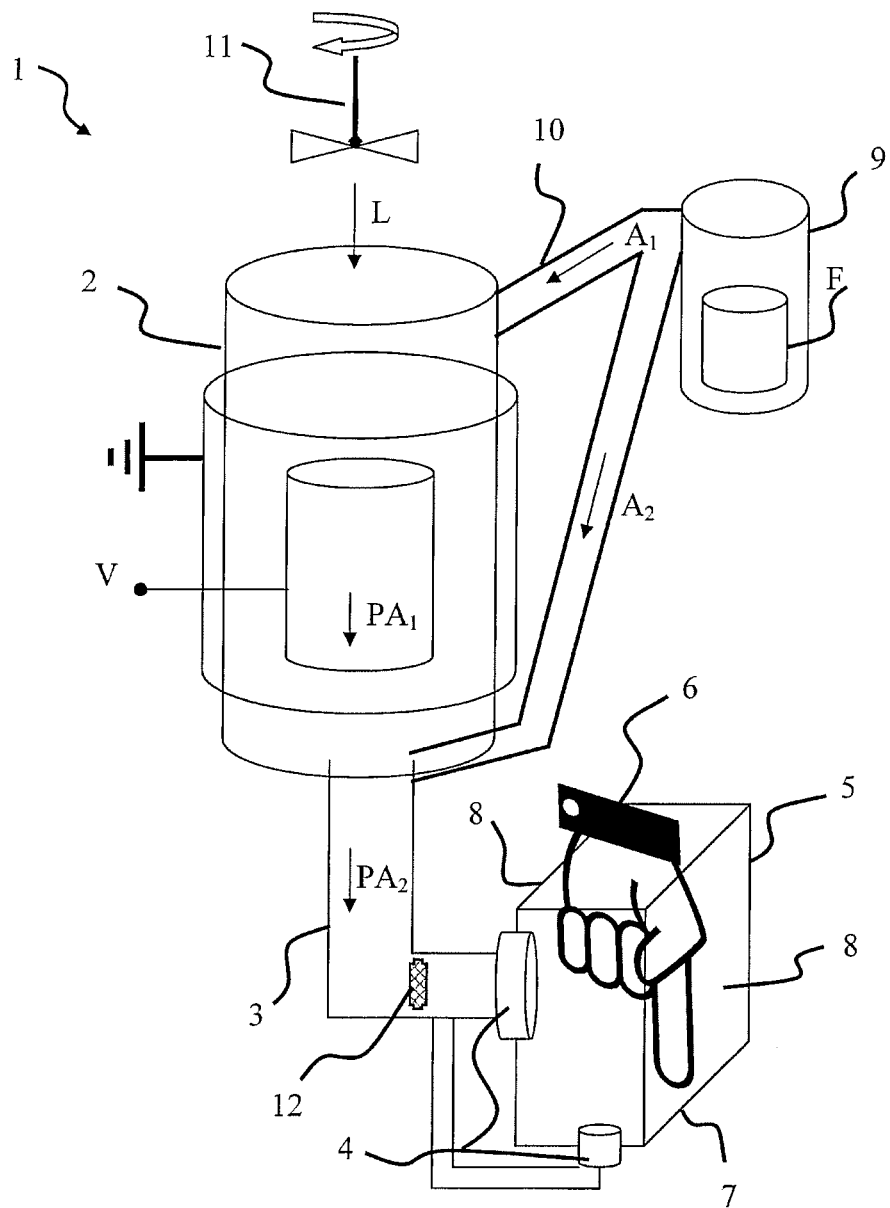
FIG. 3 shows a sketch of a third embodiment of a disinfection device for plasma disinfection.

In FIG. 3, it is possible to identify a third embodiment of the disinfection device 1, which is a combination of the first and second embodiment in accordance with FIGS. 1 and 2. In this case, a partial aerosol stream $A_1$ is guided into the inlet of the plasma generator 2 and another partial aerosol stream $A_2$ is guided to the outlet of the plasma generator 2. The plasma gas stream $PA_1$ already containing aerosols, generated by the plasma generator 2, is processed further by the further addition of the aerosol stream $A_2$.

Figure 4:
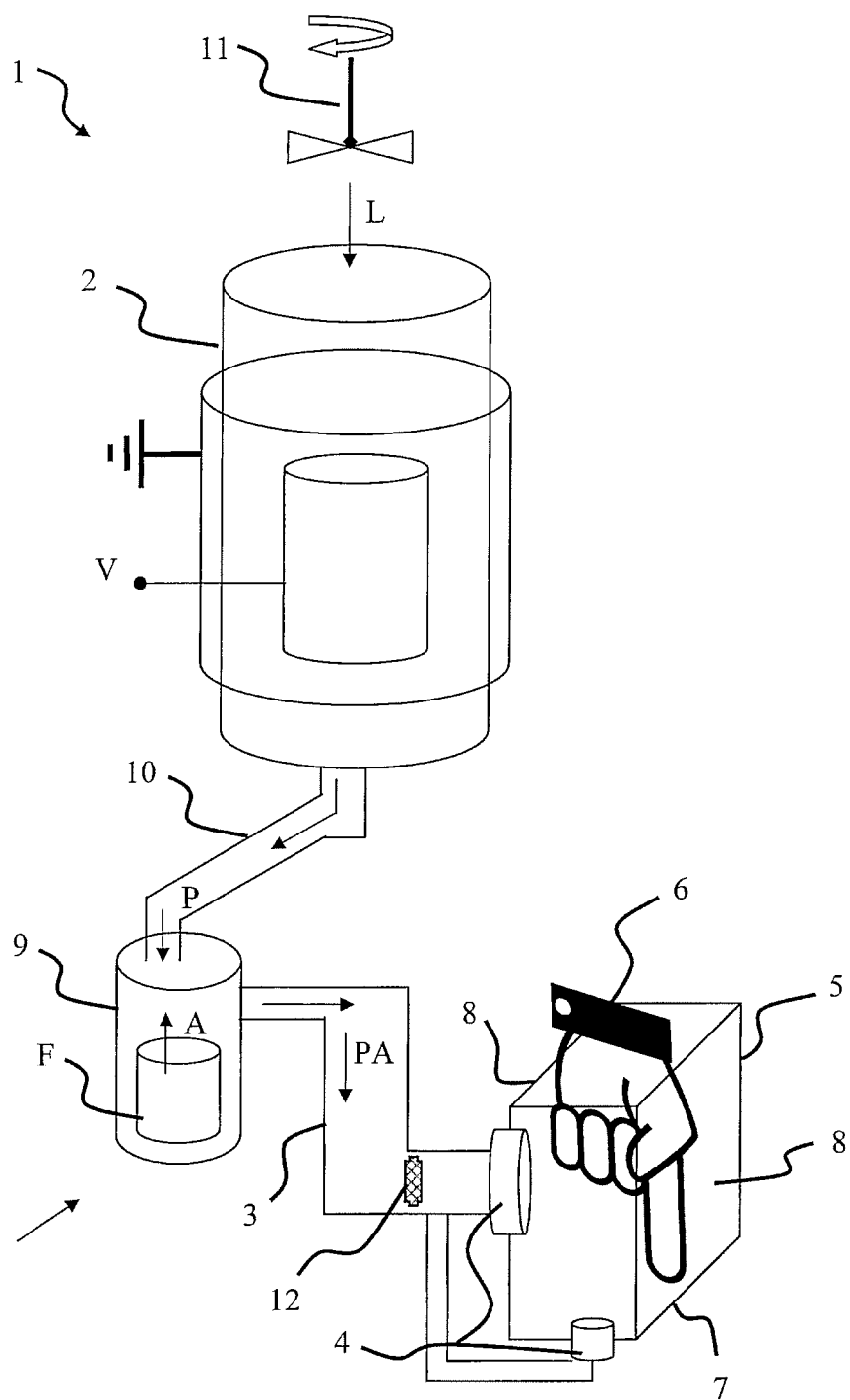
FIG. 4 shows a sketch of a fourth embodiment of a disinfection device for plasma disinfection.

FIG. 4 shows a fourth embodiment of a disinfection device 1, which is comparable, in principle, with the above-described embodiments. However, in this embodiment, the plasma gas stream P is guided through the aerosol generator 9 and the aerosol is introduced into the plasma gas stream P directly during the generation of the aerosol, e.g. by ultrasonic atomization, in order to obtain the aerosol-containing plasma gas stream PA.

The round electrode cross section sketched-out in FIGS. 1 to 4 is preferable. Ideally, other cross sections, such as, in particular, rectangular or square ones, are conceivable.

The disinfection process can be optimized by regulating the process parameters of the flow speed of the air stream L, the plasma stream P and/or the aerosol stream A and the partial streams $A_1$, $A_2$ thereof, the electrode spacings, the droplet size of the aerosols, the degree of saturation of the aerosols in the plasma stream P, the electric current and the electric voltage for the plasma generation, etc.

Figure 5:
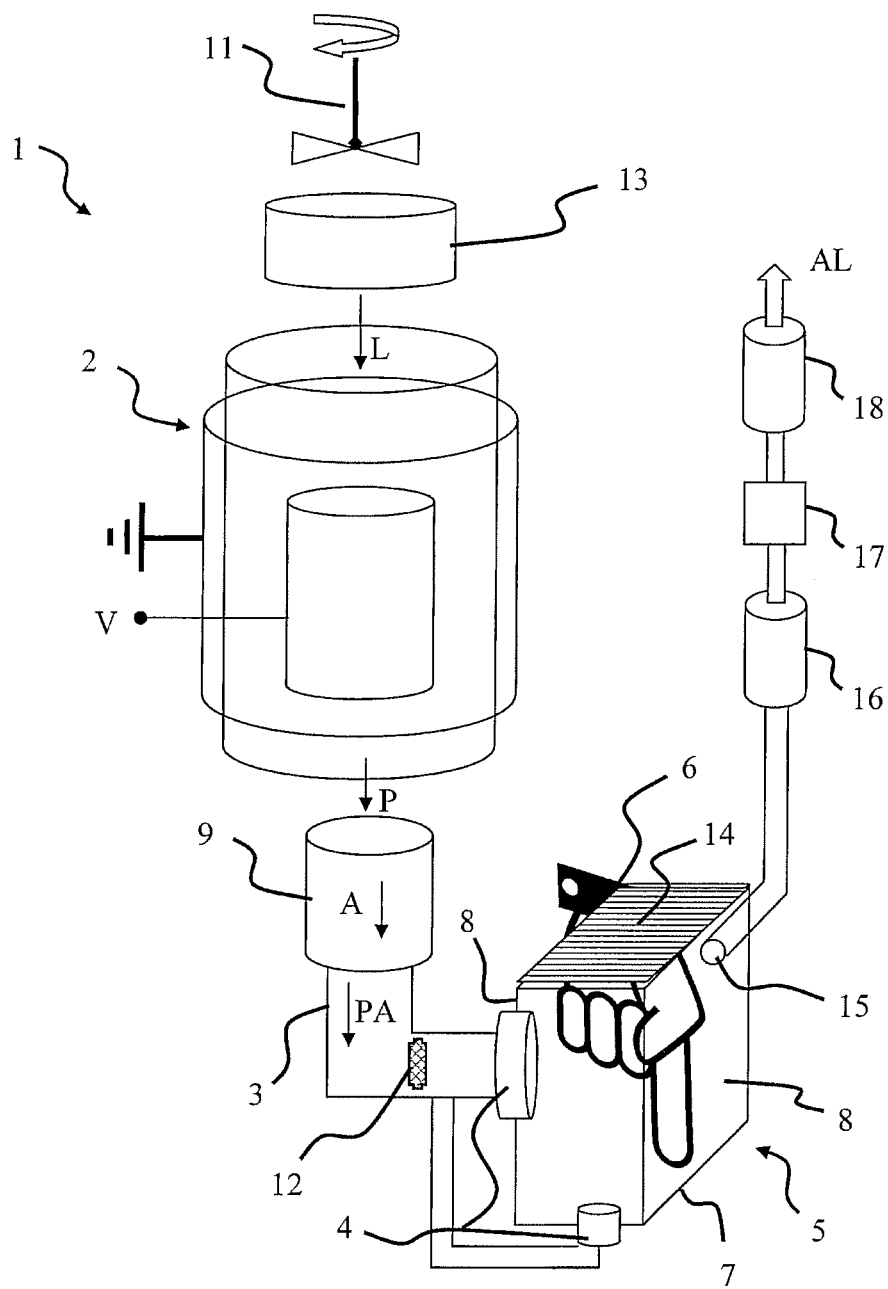
FIG. 5 shows a sketch of a fifth embodiment of a disinfection device for plasma disinfection.

In FIG. 5, it is possible to identify a sketch of a fifth embodiment of a disinfection device 1 for plasma disinfection. In principle, it is based on the first embodiment in accordance with FIG. 1, and so reference can be made to the explanations found there. However, it is complemented to the extent that the air stream L guided into the plasma generator 2 is guided with the aid of an air dryer 13 for pre-drying the air stream L. By way of example, a cartridge filled with silica gel is suitable as an air dryer, the inlet of which is connected to a membrane pump for pumping air from the atmosphere into the air dryer 13. The outlet of the cartridge is then connected to the inlet of the plasma generator 2, for example by way of a tube line.

The outlet of the plasma generator 2 is communicatively connected to the aerosol generator 9, for example by way of a tube line, in such a way that the plasma gas stream P is guided through the aerosol generator 9. In the process, the plasma gas stream P is moistened with the aerosol A in order to form a moist plasma gas stream PA. The latter is then guided into the treatment space, i.e. the disinfection region 5.

The disinfection region 5 which is closed-off by side walls 8 along the circumferential side and by a base 7 is only open to one side for the insertion of the hand 6 of a person. By way of suitable air nozzles, this open side has an air curtain 14, by means of which the disinfection region 5, i.e. the treatment space, is sufficiently well closed-off despite the inserted hand 6 and the arm of a person protruding therefrom. The air nozzles are preferably embodied as air knives, which generate an emerging air stream with a very narrow form and can have virtually any width, corresponding to the width of the opening of the treatment space. The air gap of the air curtain is preferably so narrow that it lies in the region of 0.5 to 0.8 mm. The amount of air required for the air curtain 14 is guided with a defined pressure through the at least one air knife. In this case, the air knife has a long, narrow slit and generates a knife-like air curtain 14 with a constant high air speed. The start and the end of the air curtain 14 have relatively the same length.

Furthermore, provision is made in this embodiment for the disinfection region 5, i.e. the treatment space, to have an outlet 15, by means of which a condensate separator 16 and a further air dryer 17 are communicatively connected e.g. by way of a tube line. An air suctioning pump 19, e.g. in the form of a membrane pump, is coupled to the outlet of the air dryer 17 in order to withdraw plasma-activated air introduced into the treatment space 5 from the treatment space 5 again after the treatment. The condensate separator 16, which e.g. can be realized with Peltier cooling, is then used to reduce the moisture content for sparing the air dryer 17. The exhaust air dried by the air dryer 17 is then fed to an ozone catalyzer 18 in order to reduce the portion of ozone from the exhaust air AL.

A different apparatus, by means of which the ozone component can be reduced, i.e. by means of which ozone is largely destroyed in the exhaust gas, is also suitable in place of an ozone catalyzer 18.

As described above, an ultrasonic aerosol generator is suitable as an aerosol generator 9, in particular if it ensures particularly fine atomization with a mean particle size in the region of 4 µm and less. However, the use of humidifiers, as are used, in terms of principle of operation, to humidify the air in a room, is also conceivable.

Figure 6:
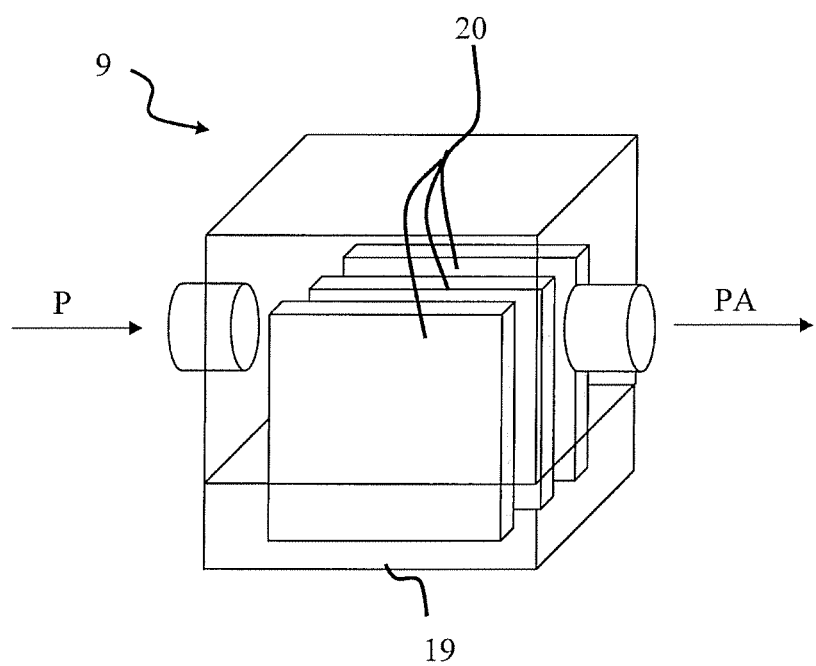
FIG. 6 shows a sketch of an aerosol generator with sintered plates for molecular moistening of the plasma gas stream.

An aerosol generator 9 for molecular moistening of the plasma gas stream P by virtue of the plasma gas stream P being guided past humidifying surfaces 20 is particularly suitable. Such an aerosol generator 9 with a plurality of sintered plates is sketched in FIG. 6. By way of example, the humidifying surfaces 20 are PE sintered plates or other filter plates with a defined porosity, which stand in a bath 19 filled with ion-free or reduced-ion water. The plasma gas stream P then flows around the plate portion of the at least one sintered plate 20 protruding from the bath 19. When the plasma gas stream P sweeps past, the at least one humidified sintered plate 20 gives off humidity to this air stream. The plasma gas stream P has as a result a relatively high relative air humidity. The fluid used to humidify the at least one sintered plate 20 can be introduced into the bath 19 by the pump effect of the sintered plates 20 without pumps due to the capillary effect of the sintered plates 20. The humidifying surface 20, e.g. in the form of a PE plate made of sintering material, which has capillaries, preferably stands with approximately 1/10 of the height thereof in a bath 19 of ion-free water. The sintered plates 20 preferably have a thickness of approximately 2 mm+/−1 mm.

A heater 12 for warming the fluid (preferably pure water) is preferably present at the base of the aerosol generator 9.

In all embodiments described above, the disinfection region 5 is preferably arranged above the aerosol generator 9 and the plasma generator 2 such that the plasma stream PA mixed with the aerosol flows up into the disinfection region 5 against gravity. As a consequence, the condensate flows back into the aerosol generator 9 and substantially does not even reach the disinfection space 5.

The invention claimed is:

1. A disinfection device for plasma disinfection of a surface, comprising:
    a plasma generator for generating a disinfecting plasma gas stream, said plasma generator comprising a plasma gas stream outlet;
    an at least partly closed disinfection region which is communicatively connected to the plasma generator and which is embodied to receive the surface to be disinfected;
    an aerosol generator for generating an aerosol stream containing aqueous particles, wherein the aerosol generator is coupled to the plasma gas stream outlet of the plasma generator in order to mix the plasma gas stream generated by the plasma generator with the aerosol stream of the aerosol generator and to subsequently guide the plasma gas stream mixed with the aerosol stream into the disinfection region and onto the surface to be disinfected.

2. The disinfection device as claimed in claim 1, wherein the aerosol generator has an atomizer unit for atomizing a fluid.

3. The disinfection device as claimed in claim 2, wherein the atomizer unit has an ultrasonic atomizer.

4. The disinfection device as claimed in claim 2 wherein the fluid is an emulsion-containing liquid.

5. The disinfection device as claimed in claim 1, wherein the aerosol generator has at least one humidifying surface, which is connected with fluid for moistening the humidifying surface and which is arranged actuatable by an air stream in such a way that the air stream sweeping past the at least one humidifying surface is moistened and mixed with the plasma gas stream as aerosol stream.

6. The disinfection device as claimed in claim 5, wherein the at least one humidifying surface is embodied as a plate having capillaries, which plate stands in a fluid bath and the plate portion thereof protruding out of the fluid bath can be actuated by the air stream.

7. The disinfection device as claimed claim 1, wherein the disinfection device has a fan, which is communicatively connected to the disinfection region in order to guide an air stream into the disinfection region.

8. The disinfection device as claimed in claim 7, wherein the fan is connected to a heating apparatus for heating the air stream caused by the fan.

9. The disinfection device as claimed in claim 7, wherein the fan is communicatively connected to the plasma generator for guiding an air stream caused by the fan through the plasma generator.

10. The disinfection device as claimed in claim 1, wherein the disinfection region is embodied to receive at least one hand to be disinfected of a person and to disinfect the surface of the hand at least received in the disinfection region.

11. The disinfection device as claimed in claim 1, wherein the disinfection region has an opening for receiving the surface to be disinfected, which opening can be closed-off from the surroundings by an air curtain, which is formed by at least one air stream emerging from an air nozzle.

12. The disinfection device as claimed in claim 1, wherein the disinfection region is communicatively connected to an arrangement for suctioning away air, wherein the arrangement for suctioning away air is configured to lead away the plasma gas stream mixed with the aerosol stream which is introduced into the disinfection region and wherein the arrangement for suctioning away air has an ozone catalyzer for neutralizing ozone situated in the suctioned-away air stream.

13. A method for plasma disinfection of a surface, comprising:
    generating a disinfecting plasma gas stream;
    mixing an aerosol stream containing aqueous particles with the plasma gas stream to produce a plasma gas stream containing aqueous aerosol particles; and
    guiding the plasma gas stream containing aqueous aerosol particles into an at least partly closed disinfection region and onto the surface to be disinfected, wherein the surface to be disinfected is received in the disinfection region.

14. The method as claimed in claim 13, further comprising:
    ultrasonic atomization of a liquid to produce the aqueous aerosol stream; and
    introducing the aqueous aerosol stream atomized by ultrasound into the plasma gas stream after the generation of the plasma gas stream for the purposes of mixing the aerosol stream with the plasma gas stream.

15. The method as claimed in claim 13, further comprising molecular moistening of an air stream to form the aerosol stream.

16. The method as claimed in claim 13, further comprising pre-drying of an air stream introduced into a plasma generator which generates the plasma gas stream.

* * * * *